United States Patent
Brownell et al.

(10) Patent No.: US 10,722,400 B2
(45) Date of Patent: *Jul. 28, 2020

(54) HYBRID OPHTHALMIC INTERFACE APPARATUS AND METHOD OF INTERFACING A SURGICAL LASER WITH AN EYE

(71) Applicant: AMO Development, LLC, Santa Ana, CA (US)

(72) Inventors: Michael F. Brownell, San Clemente, CA (US); Jim Hill, Santa Ana, CA (US)

(73) Assignee: AMO Development, LLC, Santa Ana, CA (US)

(*) Notice: Subject to any disclaimer, the term of this patent is extended or adjusted under 35 U.S.C. 154(b) by 190 days.

This patent is subject to a terminal disclaimer.

(21) Appl. No.: 15/796,685

(22) Filed: Oct. 27, 2017

(65) Prior Publication Data

US 2018/0049917 A1  Feb. 22, 2018

Related U.S. Application Data

(62) Division of application No. 13/230,590, filed on Sep. 12, 2011, now abandoned.

(51) Int. Cl.
| | | |
|---|---|---|
| A61F 9/00 | (2006.01) | |
| A61F 9/009 | (2006.01) | |
| A61B 3/117 | (2006.01) | |
| A61B 3/125 | (2006.01) | |
| A61B 17/30 | (2006.01) | |
| A61F 9/008 | (2006.01) | |

(52) U.S. Cl.
CPC .............. *A61F 9/009* (2013.01); *A61B 3/117* (2013.01); *A61B 3/125* (2013.01); *A61B 2017/306* (2013.01); *A61F 2009/00872* (2013.01)

(58) Field of Classification Search
CPC ........... A61F 9/009; A61F 2009/00872; A61B 3/117; A61B 3/125; A61B 2017/306
See application file for complete search history.

(56) References Cited

U.S. PATENT DOCUMENTS

| | | | |
|---|---|---|---|
| 1,483,509 A | 2/1924 | Bugbee | |
| 2,129,305 A | 9/1938 | William | |
| 2,274,142 A | 2/1942 | Houchin | |
| 2,405,989 A | 8/1946 | Beach | |

(Continued)

FOREIGN PATENT DOCUMENTS

| | | |
|---|---|---|
| AU | 3225789 A1 | 10/1989 |
| CH | 681687 A5 | 5/1993 |

(Continued)

OTHER PUBLICATIONS

Amo Specs Model AC-21B, AMO Classic Series, 1992, 1 page.
(Continued)

*Primary Examiner* — Eric D. Bertram
(74) *Attorney, Agent, or Firm* — Johnson & Johnson Surgical Vision, Inc.

(57) ABSTRACT

Apparatus and methods are provided for interfacing a surgical laser with an eye using a patient interface device that minimizes aberrations through a combination of a contact lens surface positioning and a liquid medium between an anterior surface of the eye and the contact lens surface.

2 Claims, 8 Drawing Sheets

(56) References Cited

U.S. PATENT DOCUMENTS

| | | |
|---|---|---|
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | William |
| 3,339,997 A | 9/1967 | Wesley |
| 3,420,006 A | 1/1969 | Howard |
| 3,431,327 A | 3/1969 | George |
| 3,482,906 A | 12/1969 | David |
| 3,542,461 A | 11/1970 | Louis et al. |
| 3,673,616 A | 7/1972 | Fedorov et al. |
| 3,693,301 A | 9/1972 | Lemaitre |
| 3,711,870 A | 1/1973 | Deitrick |
| 3,718,870 A | 2/1973 | Keller |
| 3,794,414 A | 2/1974 | Wesley |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 4,010,496 A | 3/1977 | Neefe |
| 4,014,049 A | 3/1977 | Richards et al. |
| 4,041,552 A | 8/1977 | Ganias |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy et al. |
| 4,087,866 A | 5/1978 | Choyce et al. |
| 4,110,848 A | 9/1978 | Jensen |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,442,553 A | 4/1984 | Hessburg |
| 4,463,458 A | 8/1984 | Seidner |
| 4,476,591 A | 10/1984 | Arnott |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,661,108 A | 4/1987 | Grendahl |
| 4,664,666 A | 5/1987 | Barrett |
| 4,676,792 A | 6/1987 | Praeger |
| 4,687,484 A | 8/1987 | Kaplan |
| 4,693,572 A | 9/1987 | Tsuetaki |
| 4,693,716 A | 9/1987 | MacKool |
| RE32,525 E | 10/1987 | Pannu |
| 4,702,244 A | 10/1987 | Mazzocco |
| 4,704,016 A | 11/1987 | De Carle |
| 4,710,194 A | 12/1987 | Kelman |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Reiland |
| 4,830,481 A | 5/1989 | Futhey et al. |
| 4,840,627 A | 6/1989 | Blumenthal |
| 4,842,601 A | 6/1989 | Smith |
| 4,878,910 A | 11/1989 | Koziol et al. |
| 4,878,911 A | 11/1989 | Anis |
| 4,881,804 A | 11/1989 | Cohen |
| 4,888,012 A | 12/1989 | Horn et al. |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,946,469 A | 8/1990 | Sarfarazi |
| 4,955,902 A | 9/1990 | Kelman |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,009,660 A | 4/1991 | Clapham |
| 5,019,098 A | 5/1991 | Mercier |
| 5,019,099 A | 5/1991 | Nordan |
| 5,047,051 A | 9/1991 | Cumming |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |

(56) References Cited

U.S. PATENT DOCUMENTS

| | | |
|---|---|---|
| 5,141,506 A | 8/1992 | York |
| 5,147,397 A | 9/1992 | Christ et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,171,254 A | 12/1992 | Sher |
| 5,171,266 A | 12/1992 | Wiley et al. |
| 5,173,723 A | 12/1992 | Volk |
| 5,174,254 A | 12/1992 | Humburg |
| 5,192,317 A | 3/1993 | Kalb |
| 5,192,318 A | 3/1993 | Schneider et al. |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,282,088 A | 1/1994 | Davidson |
| 5,336,215 A | 8/1994 | Hsueh et al. |
| 5,354,335 A | 10/1994 | Lipshitz et al. |
| 5,359,373 A | 10/1994 | Koester et al. |
| RE34,988 E | 7/1995 | Yang et al. |
| 5,437,658 A | 8/1995 | Muller et al. |
| 5,443,506 A | 8/1995 | Garabet |
| 5,476,514 A | 12/1995 | Cumming |
| 5,480,428 A | 1/1996 | Fedorov |
| 5,489,302 A | 2/1996 | Skottun |
| 5,496,366 A | 3/1996 | Cumming |
| 5,521,656 A | 5/1996 | Portney |
| 5,548,352 A | 8/1996 | Dewey |
| 5,549,632 A | 8/1996 | Lai |
| 5,556,417 A | 9/1996 | Sher |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,784,147 A | 7/1998 | Volk |
| 5,807,379 A | 9/1998 | L'Esperance, Jr. |
| 5,814,103 A | 9/1998 | Lipshitz et al. |
| 5,824,074 A | 10/1998 | Koch |
| 5,843,188 A | 12/1998 | McDonald |
| 5,847,802 A | 12/1998 | Menezes et al. |
| 5,876,442 A | 3/1999 | Lipshitz et al. |
| 5,898,473 A | 4/1999 | Seidner et al. |
| 5,968,094 A | 10/1999 | Werblin et al. |
| 5,984,915 A | 11/1999 | Loeb et al. |
| 5,984,916 A | 11/1999 | Lai |
| 5,997,559 A | 12/1999 | Ziemer |
| 6,013,101 A | 1/2000 | Israel |
| 6,051,024 A | 4/2000 | Cumming |
| 6,083,261 A | 7/2000 | Callahan et al. |
| 6,096,078 A | 8/2000 | McDonald |
| 6,110,202 A | 8/2000 | Barraquer et al. |
| 6,117,171 A | 9/2000 | Skottun |
| 6,136,026 A | 10/2000 | Israel |
| 6,140,630 A | 10/2000 | Rhodes |
| 6,152,958 A | 11/2000 | Nordan |
| 6,176,878 B1 | 1/2001 | Gwon et al. |
| 6,197,058 B1 | 3/2001 | Portney |
| 6,200,342 B1 | 3/2001 | Tassignon |
| 6,217,612 B1 | 4/2001 | Woods |
| 6,228,115 B1 | 5/2001 | Hoffmann et al. |
| 6,231,603 B1 | 5/2001 | Lang et al. |
| 6,247,473 B1 | 6/2001 | Yavitz |
| 6,254,595 B1 | 7/2001 | Juhasz et al. |
| 6,299,641 B1 | 10/2001 | Woods |
| 6,302,911 B1 | 10/2001 | Hanna |
| 6,322,589 B1 | 11/2001 | Cumming |
| 6,325,792 B1 | 12/2001 | Swinger et al. |
| 6,373,571 B1 | 4/2002 | Juhasz et al. |
| 6,399,734 B1 | 6/2002 | Hodd et al. |
| 6,406,494 B1 | 6/2002 | Laguette et al. |
| 6,436,113 B1 | 8/2002 | Burba et al. |
| 6,443,985 B1 | 9/2002 | Woods |
| 6,485,516 B2 | 11/2002 | Boehm |
| 6,488,708 B2 | 12/2002 | Sarfarazi |
| 6,503,276 B2 | 1/2003 | Lang et al. |
| 6,524,340 B2 | 2/2003 | Israel |
| 6,551,354 B1 | 4/2003 | Ghazizadeh et al. |
| 6,554,859 B1 | 4/2003 | Lang et al. |
| 6,558,420 B2 | 5/2003 | Green |
| 6,559,317 B2 | 5/2003 | Hupperts et al. |
| 6,592,621 B1 | 7/2003 | Domino |
| 6,599,317 B1 | 7/2003 | Weinschenk, III et al. |
| 6,616,691 B1 | 9/2003 | Tran |
| 6,616,692 B1 | 9/2003 | Glick et al. |
| 6,623,476 B2 | 9/2003 | Kurtz et al. |
| 6,638,305 B2 | 10/2003 | Laguette |
| 6,638,306 B2 | 10/2003 | Cumming |
| 6,645,246 B1 | 11/2003 | Weinschenk, III |
| 6,660,035 B1 | 12/2003 | Lang et al. |
| 6,676,653 B2 | 1/2004 | Juhasz et al. |
| 6,749,633 B1 | 6/2004 | Lorenzo et al. |
| 6,749,634 B2 | 6/2004 | Hanna |
| 6,855,164 B2 | 2/2005 | Glazier |
| 6,863,667 B2 * | 3/2005 | Webb ............ A61F 9/009 606/166 |
| 6,899,707 B2 | 5/2005 | Scholler et al. |
| 7,018,376 B2 | 3/2006 | Webb et al. |
| 7,018,409 B2 | 3/2006 | Glick et al. |
| 7,025,783 B2 | 4/2006 | Brady et al. |
| 7,097,660 B2 | 8/2006 | Portney |
| 7,125,422 B2 | 10/2006 | Woods et al. |
| 7,150,759 B2 | 12/2006 | Paul et al. |
| 7,220,279 B2 | 5/2007 | Nun |
| 7,223,288 B2 | 5/2007 | Zhang et al. |
| 7,371,230 B2 * | 5/2008 | Webb ............ A61F 9/009 606/166 |
| 7,503,938 B2 | 3/2009 | Phillips |
| 7,611,507 B2 | 11/2009 | Raksi et al. |
| 2002/0103481 A1 | 8/2002 | Webb et al. |
| 2002/0111678 A1 | 8/2002 | Zadno-Azizi et al. |
| 2002/0116058 A1 | 8/2002 | Zadno-Azizi et al. |
| 2002/0120329 A1 | 8/2002 | Lang et al. |
| 2002/0167644 A1 | 11/2002 | Pollack et al. |
| 2002/0188351 A1 | 12/2002 | Laguette |
| 2003/0060878 A1 | 3/2003 | Shadduck |
| 2003/0060881 A1 | 3/2003 | Glick et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0187505 A1 | 10/2003 | Liao |
| 2003/0204254 A1 | 10/2003 | Peng et al. |
| 2003/0204255 A1 | 10/2003 | Peng et al. |
| 2004/0054408 A1 | 3/2004 | Glick et al. |
| 2004/0082993 A1 | 4/2004 | Woods |
| 2004/0111153 A1 | 6/2004 | Woods et al. |
| 2004/0158322 A1 | 8/2004 | Shen |
| 2004/0167621 A1 | 8/2004 | Peyman |
| 2004/0181279 A1 | 9/2004 | Nun |
| 2004/0215340 A1 | 10/2004 | Messner et al. |
| 2005/0021139 A1 | 1/2005 | Shadduck |
| 2005/0027354 A1 | 2/2005 | Brady et al. |
| 2005/0085906 A1 | 4/2005 | Hanna |
| 2005/0085907 A1 | 4/2005 | Hanna |
| 2005/0125057 A1 | 6/2005 | Cumming |
| 2005/0131535 A1 | 6/2005 | Woods |
| 2005/0137703 A1 | 6/2005 | Chen |

(56) References Cited

U.S. PATENT DOCUMENTS

| | | |
|---|---|---|
| 2005/0143718 A1 | 6/2005 | Rathjen |
| 2005/0192562 A1 | 9/2005 | Loesel et al. |
| 2005/0248724 A1 | 11/2005 | Jones |
| 2005/0288785 A1 | 12/2005 | Portney et al. |
| 2006/0064162 A1 | 3/2006 | Klima |
| 2006/0111776 A1 | 5/2006 | Glick et al. |
| 2006/0116765 A1 | 6/2006 | Blake et al. |
| 2006/0192921 A1 | 8/2006 | Loesel et al. |
| 2007/0067872 A1 | 3/2007 | Mittendorf et al. |
| 2007/0078515 A1 | 4/2007 | Brady |
| 2007/0093795 A1 | 4/2007 | Melcher et al. |
| 2007/0093796 A1 | 4/2007 | Raksi et al. |
| 2007/0106381 A1 | 5/2007 | Blake |
| 2007/0123591 A1 | 5/2007 | Kuppuswamy |
| 2007/0129798 A1 | 6/2007 | Chawdhary |
| 2007/0135915 A1 | 6/2007 | Klima |
| 2007/0173794 A1 | 7/2007 | Frey et al. |
| 2007/0299487 A1 | 12/2007 | Shadduck |
| 2008/0103367 A1 | 5/2008 | Burba et al. |
| 2008/0161913 A1 | 7/2008 | Brady et al. |
| 2008/0161914 A1 | 7/2008 | Brady et al. |
| 2009/0012609 A1 | 1/2009 | Geraghty et al. |
| 2010/0274228 A1* | 10/2010 | Mrochen ................ A61F 9/009 604/541 |
| 2011/0022035 A1 | 1/2011 | Porter et al. |

FOREIGN PATENT DOCUMENTS

| | | |
|---|---|---|
| DE | 2702117 A1 | 7/1978 |
| DE | 3246306 A1 | 6/1984 |
| DE | 4038088 A1 | 6/1992 |
| DE | 19501444 A1 | 7/1996 |
| EP | 64812 A2 | 11/1982 |
| EP | 246216 A2 | 11/1987 |
| EP | 328117 A2 | 8/1989 |
| EP | 329981 A1 | 8/1989 |
| EP | 0337390 A2 | 10/1989 |
| EP | 342895 A2 | 11/1989 |
| EP | 351471 A2 | 1/1990 |
| EP | 356050 A1 | 2/1990 |
| EP | 488835 A1 | 6/1992 |
| EP | 507292 A1 | 10/1992 |
| EP | 566170 A1 | 10/1993 |
| EP | 601845 A1 | 6/1994 |
| EP | 691109 A1 | 1/1996 |
| EP | 897702 A2 | 2/1999 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| WO | 8603961 A1 | 7/1986 |
| WO | 8700299 A1 | 1/1987 |
| WO | 8707496 A1 | 12/1987 |
| WO | 8902251 A1 | 3/1989 |
| WO | 8911672 A1 | 11/1989 |
| WO | 9000889 A1 | 2/1990 |
| WO | 9305733 A1 | 4/1993 |
| WO | 9610968 A1 | 4/1994 |
| WO | 9416648 A1 | 8/1994 |
| WO | 9503783 A1 | 2/1995 |
| WO | 9615712 A1 | 5/1996 |
| WO | 9615734 A2 | 5/1996 |
| WO | 9625126 A1 | 8/1996 |
| WO | 9712272 A1 | 4/1997 |
| WO | 9727825 A1 | 8/1997 |
| WO | 9743984 A1 | 11/1997 |
| WO | 9807053 A2 | 2/1998 |
| WO | 9856315 A1 | 12/1998 |
| WO | 0027315 A1 | 5/2000 |
| WO | 0061036 A1 | 10/2000 |
| WO | 0066039 A1 | 11/2000 |
| WO | 0119288 A1 | 3/2001 |
| WO | 0134066 A1 | 5/2001 |
| WO | 0134067 A1 | 5/2001 |
| WO | 0144871 A1 | 6/2001 |
| WO | 0219949 A2 | 3/2002 |
| WO | 03015669 A1 | 2/2003 |
| WO | 03034949 A2 | 5/2003 |
| WO | 03059208 A2 | 7/2003 |
| WO | 03075810 A1 | 9/2003 |
| WO | 05018504 A1 | 3/2005 |
| WO | 2007040964 A1 | 4/2007 |
| WO | 2007050572 A2 | 5/2007 |
| WO | 2007067872 A2 | 6/2007 |
| ZA | 0888414 | 11/1988 |

OTHER PUBLICATIONS

Dynasil Corporation, "Precision Optics Materials Fabrication." Retrieved from the Internet: URL: http://www.dynasil.com, 3 pages.

Dynasil Optical Property, Information on the Optical Properties of Dynasil Synthetic Fused Silica, available at least as early as May 30, 2001, 2 pages.

Dynasil Technical Resources, Specifications on Lens Material from Dynasil Website, available at least as early as May 19, 2001, 3 pages.

Edmund Optics, Tech Spec for Fused silica windows, High Performance UV Optics-PCV; High Performance UV Optics-DCV; High Performance UV Optics-DCX; and High Performance UV Optics-PCX, Retrieved from the interne: URL: http://www.edmundoptics.com/online ctalog/search/index.cfm, 17 pages.

Fechner P.U., et al., "Iris-Claw Lens in Phakic Eyes to Correct Hyperopia: Preliminary Study," Journal of Cataract and Refractive Surgery, 1998, vol. 24 (1), pp. 48-56.

International Preliminary Examination Report for Application No. PCT/US02120294, dated Aug. 25, 2003, 7 pages.

International Preliminary Report on Patentability and Written Opinion for Application No. PCT/US08/084816, dated Jun. 31, 2010, 9 pages.

International Search Report for Application No. PCT/US02/20294, dated Sep. 12, 2002, 1 page.

International Search Report for Application No. PCT/US08/084816, dated Jul. 3, 2009, 5 pages.

Ito M., et al., "Picosecond Laser in Situ Keratomileusis with a 1053-nm Nd: YLF Laser," Journal of Refractive Surgery, 1996, vol. 12 (6), pp. 721-728.

Juhasz T., et al., "Corneal Refractive Surgery with Femtosecond Lasers," IEEE Journal of Selected Topics in Quantum Electronics, 1999, vol. 5 (4), pp. 902-910.

Mandell R.B., "Contact Lens Practice", 4th Edition, Charles C. Thomas Publishers, 1988, 11 pages.

Marketing Materials for Fused Silica, 2 pages.

Menezo J.L., et al., "Endothelial Study of Iris-Claw Phakic Lens: Four Year Follow-Up," Journal of Cataract Refractive Surgery, 1998, vol. 24 (8), pp. 1039-1049.

Partial European Search Report for Application No. EP17170401, dated Sep. 25, 2017, 13 pages.

Supplementary European Search Report of EP Patent Application No. EP02746713, dated Mar. 8, 2005, 3 pages total.

Thornton S., "Accommodation in Pseudophakia," in: Percival SPB Color atlas of lens implantation, Chap. 25, St Louis, ed., Mosby, United States, 1991, pp. 159-162.

\* cited by examiner

HYBRID OPHTHALMIC INTERFACE APPARATUS AND METHOD OF INTERFACING A SURGICAL LASER WITH AN EYE

CROSS-REFERENCE TO RELATED APPLICATIONS

This application is a divisional application of U.S. patent application Ser. No. 13/230,590, filed Sep. 12, 2011, which is herein incorporated by reference in its entirety.

FIELD OF THE INVENTION

The present invention relates to ophthalmic laser surgery and, more particularly, an ophthalmic interface apparatus used to stabilize the eye of a patient with respect to a laser beam during ophthalmic surgery and system and method of interfacing the eye with a surgical laser.

BACKGROUND

In recent years, significant developments in laser technology have led to its application in the field of ophthalmic surgery. In particular, laser surgery has become the technique of choice for ophthalmic surgical applications. In certain ophthalmic laser procedures, surgeons use a mechanical device termed a microkeratome to cut a layer of the anterior surface of the cornea in order to expose the underlying corneal stroma to which the laser is applied. However, complications surrounding the use of the microkeratome with a metal blade have resulted in research into improved techniques that are performed exclusively by a laser system. Such all-laser techniques provide significant improvements over conventional mechanical devices.

Despite these advances in laser technology, the use of such systems for ophthalmic surgical procedures remains fraught with substantial mechanical limitations, particularly in the area of developing a stable interface between an incident laser beam and the eye of a patient. Ophthalmic surgery is a precision operation and requires precise coupling between the surgical tool (i.e., the laser beam) and the region to be disturbed (i.e., a portion of the patient's eye). Movement of the eye with respect to the intended focal point of the laser beam can lead to non-optimal results and might result in permanent damage to non-renewable tissue within the eye. Given that eye movement is often the result of autonomic reflex, techniques have been developed in an attempt to stabilize the position of a patient's eye with respect to an incident laser beam.

One technique used to compensate for relative eye motion with respect to an incident laser beam is to have the patient focus on a stationary target. This involves providing a visual target to the eye undergoing surgery, and requiring that the patient retain focused on the perceived target feature. While this technique has provided some benefit, the patient bears a significant burden of minimizing relative motion. This technique is also less tolerant of any significant gross autonomic reflex motions, e.g., as when the patient might be startled. In this technique, the target provides an optical interface, while the patient's conscious responses provide the feedback mechanism.

Another technique involves the use of an optical eye tracking apparatus, whereby a selected eye feature is targeted for monitoring by an optical device. As the targeted feature displaces as a result of eye movement, this displacement is characterized and fed into the incident laser beam control apparatus as a compensation signal. This technique offers a substantial improvement over the first, particularly when implemented in addition to a patient-driven target focusing mechanism. However, such systems are inordinately expensive since a second, completely independent optical path is typically provided between a patient's eye and a surgical apparatus in order to accommodate the eye tracking apparatus. Further expense and complexity is incurred since an eye tracking apparatus requires an additional software component in order to be operative, which software component must be integrated into a laser delivery system. Considerations of interoperability must be met as well as the provision for an automatic shutdown of the laser system in the event of the loss of target feature lock.

Mechanical stabilization devices have been proposed, for example, a corneal applanation device, which is the subject of U.S. patent application Ser. No. 09/172,819, filed Oct. 15, 1998, and commonly owned by the assignee of the present invention. Such a mechanical device directly couples a patient's eye to the laser's delivery system being affixed to both the laser and the anterior surface of a patient's cornea. The corneal coupling, in these devices, is typically implemented by lowering an applanation fixture over the anterior surface of the cornea under pressure. It is assumed in these forms of devices that pressure applied normal to the corneal surface will restrict conventional motion of the cornea thereby stabilizing the eye along a major access normal to the device.

However, although this assumption may hold true in a large number of cases, it certainly does not have universal application. Moreover, in the cases where it does hold, the device/cornea interface should be established with the iris centered, for best results. The actual establishment of an effective device/corneal interface is an exercise in trial-and-error, resulting in a great deal of frustration to doctor and patient, as well as considerable eye fatigue.

For ophthalmic laser procedures where eye tissue is to be photodisrupted, it is desirable to have proper focus of the laser beam to a specific focal spot in the tissue that is to be effected. Proper focus includes focal definition and proper dimensionality (i.e., the correct spot diameter and shape). To this end, it is helpful for the laser beam to be as free from aberrations as possible. In particular, for ophthalmic laser procedures involving the cornea, the spherical geometry of the cornea can introduce optical aberrations by its shape, and these are separate and distinct from aberrations that may be introduced by the laser optical system. Corneal induced aberrations can distort the definition of the focal spot of a laser beam as the beam is focused to a position within corneal tissue or deeper into the eye, such as the capsular bag or the natural lens.

Due to the spherical geometry of the anterior surface of the cornea, two specific types of aberrations are of particular importance with regard to beam distortion; spherical aberration (which relates to points on the optical axis of the laser beam) and coma which relates to points that are off-axis). Spherical aberration and coma are similar to one another in that they both arise from a failure to image or focus optical ray traces onto the same point. Spherical aberration relates to a distortion that can be characterized as radial in nature, with some radial directions being stretched while other radial directions are shrunk, converting thereby, an ideally circular spot into an elliptical spot. Coma distortion, on the other hand, implies an elongation along one radius a circle, resulting in a "comet-like" shape. Accordingly, any structure which interfaces between a curved, anterior surface of the cornea and laser delivery system will likely encounter such aberration concerns.

In view of the foregoing, it is thus evident that there is a need for a simple mechanical interface device that is able to stabilize the eye against relative motion with respect to a laser beam used for ophthalmic surgical procedures without relying on secondary mechanical considerations, such as surface tension, friction, or the like. Such a device should be able to present an optical feature to an incident laser beam in a stable, well characterized location. In addition to maintaining a proper orientation between the eye and a laser delivery system during ophthalmic laser surgery, such a device should minimize intraocular pressure during the surgical procedure. Such a device should be easy for a clinician to affix, as well as being simple and cost effective to manufacture and use.

SUMMARY OF THE INVENTION

Apparatus and methods are provided for interfacing a surgical laser with an eye. In one embodiment, a patient interface device is provided that minimizes aberrations through a combination of a contact lens surface positioning and a liquid medium between an anterior surface of the eye and the contact lens surface. In one embodiment, an interface for coupling a patient's eye to a surgical laser system includes an attachment ring configured to overlay the anterior surface of the eye, a lens cone defining a first plane surface and configured to couple to a delivery tip of the surgical laser such that the delivery tip is positionally referenced to the first plane surface, a gripper, and a chamber configured to receive a liquid. The lens cone includes an apex ring coupled to the first plane surface and an applanation lens disposed at a distal end of the apex ring and positioned in a second plane surface parallel to the first plane surface such that the delivery tip is positionally referenced to the second plane. The gripper includes a first receptacle configured to receive the attachment ring, a central orifice configured to receive the lens cone, a gripper portion, and a receiver portion, and the gripper stabilizes the relative positions of the lens cone and the attachment ring when the lens cone and attachment ring are received within the gripper. The chamber is formed by an inner surface of the attachment ring, an inner surface of the gripper portion, an inner surface of the receiver portion, and the applanation lens when the lens cone and attachment ring are received within the gripper.

In another embodiment, an interface for coupling a patient's eye to a surgical laser system includes an attachment ring configured to overlay an anterior surface of the eye, a lens cone defining a first plane surface and configured to couple to a delivery tip of the surgical laser system such that the delivery tip is positionally referenced to the first plane surface, a gripper, and a chamber configured to receive a liquid. The lens cone includes an apex ring coupled to the first plane surface, and an applanation lens disposed at a distal end of the apex ring. The gripper includes a receptacle receiving the attachment ring, a central orifice receiving the lens cone, a gripper portion, a pair of expandable jaws, and a pair of opposed lever handles coupled to the jaws. The jaws are configured to expand a diameter of the central orifice when opened and further configured to contract the diameter of the central orifice when allowed to relax. The gripper stabilizes the relative positions of the lens cone and the attachment ring when the cone and ring are received within the gripper. The lever handles are configured to apply an opening pressure to the jaws when the opposed handles are squeezed together. The chamber is formed by an inner surface of the attachment ring, an inner surface of the gripper portion, an inner surface of the jaws, and the applanation lens.

In another embodiment, a method for interfacing an eye to a surgical laser is provided including coupling a lens cone to a delivery tip of the surgical laser, coupling an attachment ring to an anterior surface of the eye, receiving a liquid into the first receptacle, positioning the lens cone in a central orifice of a gripper, and stabilizing the relative positions of the lens cone and the attachment ring with the gripper when the lens cone and attachment ring are received within the gripper. The lens cone defines a first plane surface, and the delivery tip is positionally referenced to the first plane surface. The lens cone includes an apex ring coupled to the first plane surface and an applanation lens disposed at a distal end of the apex ring and positioned in a second plane surface parallel to the first plane surface such that the delivery tip is positionally referenced to the second plane. The anterior surface of the eye and an inner surface of the attachment ring form a first receptacle. The gripper includes a second receptacle configured to receive the attachment ring, and the central orifice is configured to receive the lens cone. A chamber containing the liquid is formed by the first receptacle and the applanation lens when the lens cone and attachment ring are received within the gripper.

BRIEF DESCRIPTION OF THE DRAWINGS

These and other features, aspects and advantages of the present invention will be more fully understood when considered in connection with the following specification, appended claims and accompanying drawings wherein:

DETAILED DESCRIPTION

Conceptually, the present invention is directed to a mechanical apparatus that performs the functions of coupling the anterior surface of a target eye to a surgical laser and stabilizing the eye. The apparatus is termed mechanical because it directly couples the mechanical surface of an operative target, such as human corneal tissue, to a mechanical fixture of a surgical laser system, such as the distal tip of a laser beam's delivery system. Simply put, and in the context of a particular embodiment which will be described in greater detail below, the apparatus is affixed to the anterior surface of a human eye and is affixed to the laser delivery system.

Figure 1:
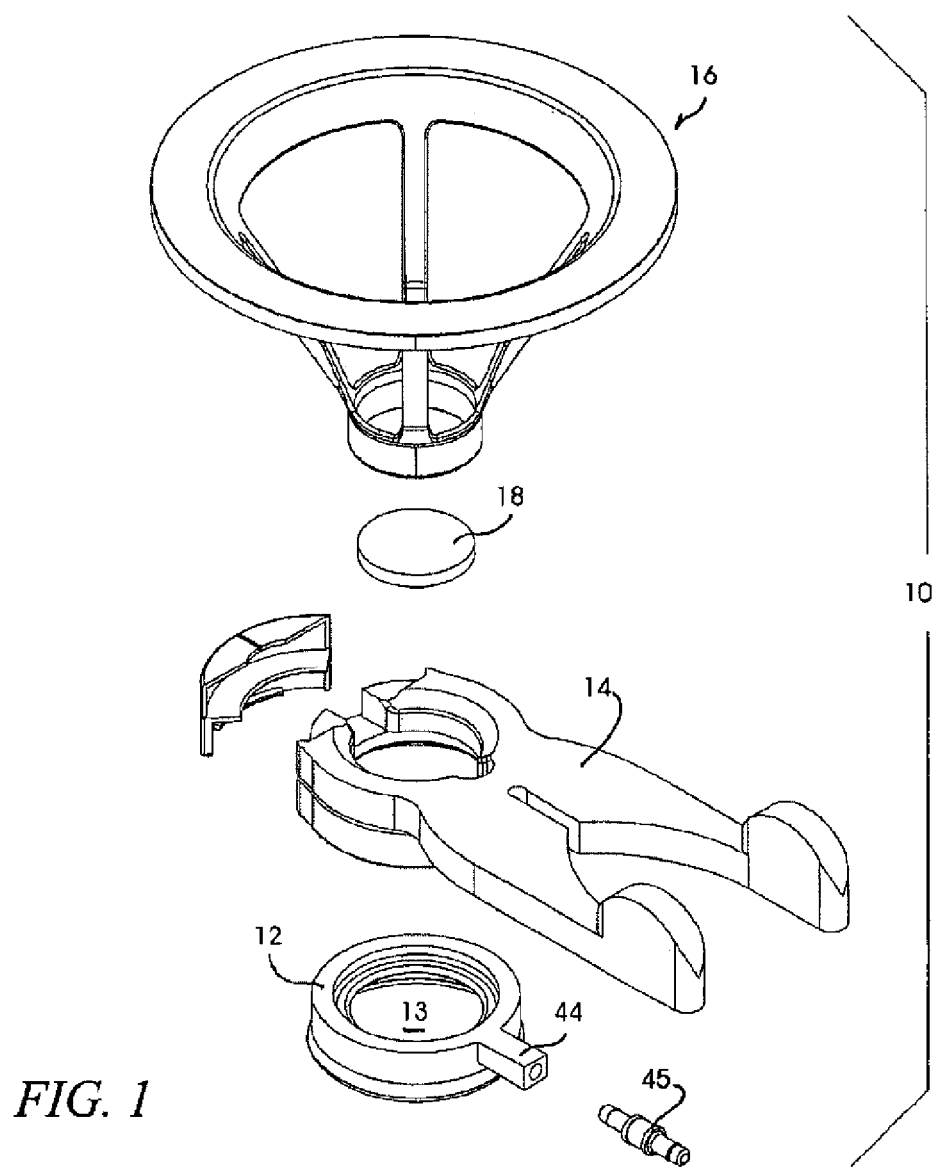
FIG. 1 is an exploded, perspective illustration of the component portions of an ocular stabilization device in accordance with one embodiment of the present invention.

Referring initially to the exemplary embodiment of FIG. 1, an illustrative ocular stablization device is shown in an exploded, perspective view, and is generally indicated at 10. The ocular stabilization device (referred to herein as simply a patient interface) is an apparatus that attaches to a human eye and holds (fixes) the eye in all three axes (x, y and z) from translational and rotational movement with respect to the incident beam of a laser surgical device. In addition, the stabilization device allows for the cornea of the eye to be applanated by a lens (laser optic) in one embodiment. The stabilization device grips, holds or affixes the eye to the applanation lens, or laser optic, during a laser surgical procedure, so as to minimize or preclude differential motion of the human eye with respect to the laser optical path during the laser procedure.

With regard to the exemplary embodiment of FIG. 1, the stabilization device 10 is comprised of a number of component parts that may be disposable (i.e., used once and discarded) and/or re-usable. In this regard, the stabilization device 10 suitably comprises an ocular attachment ring 12, by means of which the stabilization device 10 is coupled to the eye, a gripper device 14, a lens cone 16 and an applanation lens 18, which in combination with the lens cone 16 is used to establish an appropriate optical path alignment between the cornea and a laser optical path.

The component parts of the stabilization device 10 are illustrated in exploded view, and are intended to be collapsed vertically, such that each of the individual portions of the device are in mechanical engagement with appropriate other portions, such that the completed device is provided in a generally unitary structure. This is not to say that the devices' component parts are permanently affixed to one another: indeed, the component parts are separable and interchangeable at will. Rather, the stabilization device 10 is intended to form a single composite interface structure between a human cornea and a surgical laser once the component parts have been aligned with a patient's eye and with respect to the laser delivery system, as will be described in detail below.

As illustrated in the exemplary embodiment of FIG. 1, the attachment ring 12 forms the mechanical interface between the anterior surface of a human cornea and the remaining structure of the stabilization device. The attachment ring 12 is constructed of a flexible, hypoallergenic material such as rubber, hypoallergenic plastic, silicone, or the like. The attachment ring 12 is substantially annular in shape, having a generally smooth exterior surface and a highly articulated and functional inner surface, as will be described in greater detail below. Being annular in shape, the attachment ring 12 necessarily defines an outer diameter (OD) and inner diameter (ID), with the inner diameter circumscribing a central target opening 13. The absolute value of its outer diameter is not particularly relevant to practice the principles of the present invention, but the value of the inner diameter is suitably chosen such that when the attachment ring 12 is placed over a patient's eye, the attachment ring's central opening, defined by the inner diameter, completely circumscribes a sufficient area of corneal tissue such that a surgical laser procedure may be completely performed within the exposed area without having to displace the attachment ring.

The attachment ring 12 is disposed and retained within an appropriately shaped female-type receptacle 72 (FIG. 11) provided in the underside of the gripper device 14. Since the attachment ring 12 is constructed of a flexible material, the female receptacle 72 of the gripper device 14 need only have an ID of a dimension slightly smaller than the OD of the attachment ring, such that the attachment ring may fit within the receptacle and be held in place by compressive force.

Figure 2:
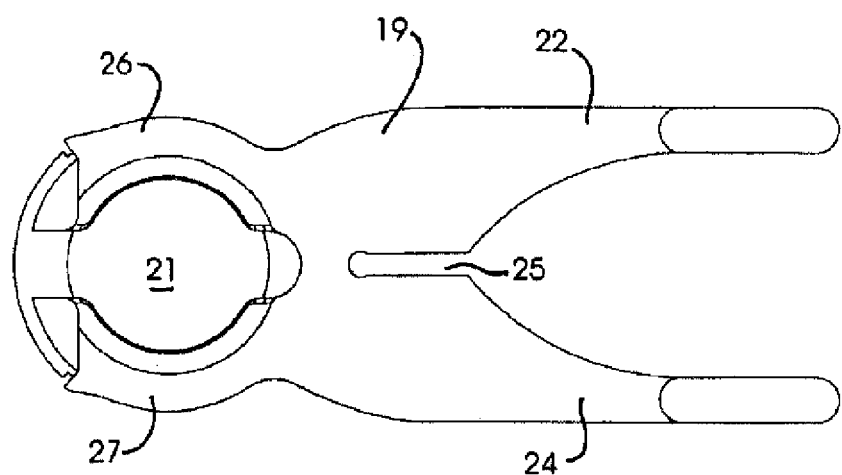
FIG. 2 is a simplified, top plan view of the gripper/interface structure suitable for use in connection with the ocular stabilization device of FIG. 1.
Figure 3:
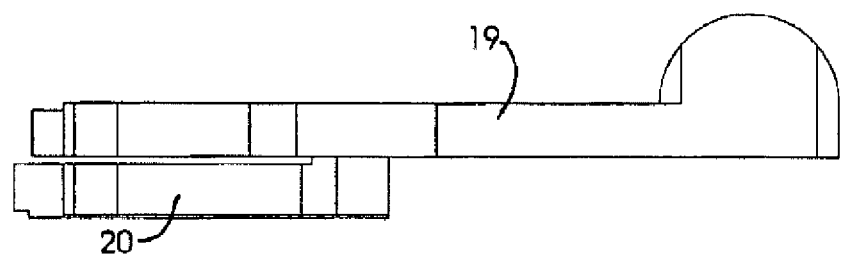
FIG. 3 is a simplified, side view of the gripper/interface structure suitable for use in connection with the ocular stabilization device of FIG. 1.

The gripper device 14 of the exemplary embodiment of FIG. 1 is detailed in the top plan view illustration of FIG. 2 and the side view illustration of FIG. 3. In general, the gripper device 14 functions much like a clothes pin, and is constructed with a gripper portion 19, overlaying a receiver portion 20 that is designed to receive and contain the attachment ring 12 within a central opening 21 that passes through both the gripper portion and the receiver portion. The gripper portion 19 is constructed as a lever, characterized by two lever handles 22 and 24 separated by a closure spacing 25, and two jaws 26 and 27 surrounding the central opening 21. As the lever handles 22 and 24 are squeezed together, the closure spacing 25 closes and a deformation force is transmitted to the jaws 26 and 27. Applying a deformation force causes the jaws 26 and 27 to further separate, in turn causing the central opening 21 to increase in area. Pinching the lever handles 22 and 24 together forces the jaws 26 and 27 to widen sufficiently for a cylindrical object to be inserted into the now-widened central opening 21. Once the pressure on the lever handles 22 and 24 is relaxed and the jaws 26 and 27 close to their nominal position, the inside surfaces of the jaws 26 and 27 compress against the object and retain the object in position in the central opening 21. This particular feature is pertinent to the present invention when it is considered that the gripper device 14 couples the attachment ring 12 to the lens cone 16 in a relatively secure manner and with a characterizable geometric relationship.

The receiver portion 20 is disposed below the jaws of the gripper portion 19 and lays in a plane parallel to that of the gripper portion. The receiver portion 20 is cantilevered forward from the space between the lever handles 22 and 24 and the jaws 26 and 27 and is separated from the jaws by a slight spacing. The receiver portion 20 is substantially annular in shape with the central opening 21 extending therethrough. Thus, it will be noted that when the jaws 26 and 27 are opened, only the central opening 21 defined in the gripper portion 19 is widened. The central opening 21 extending through the receiver portion 20 maintains its diameter.

This particular feature allows the attachment ring 12 to be maintained within the central opening 21 of the receiver portion 20, when the jaws 26 and 27 are opened. Likewise, the jaws 26 and 27 may be opened to receive, for example, the lens cone 16, without disturbing or displacing the attachment ring.

Figure 4:
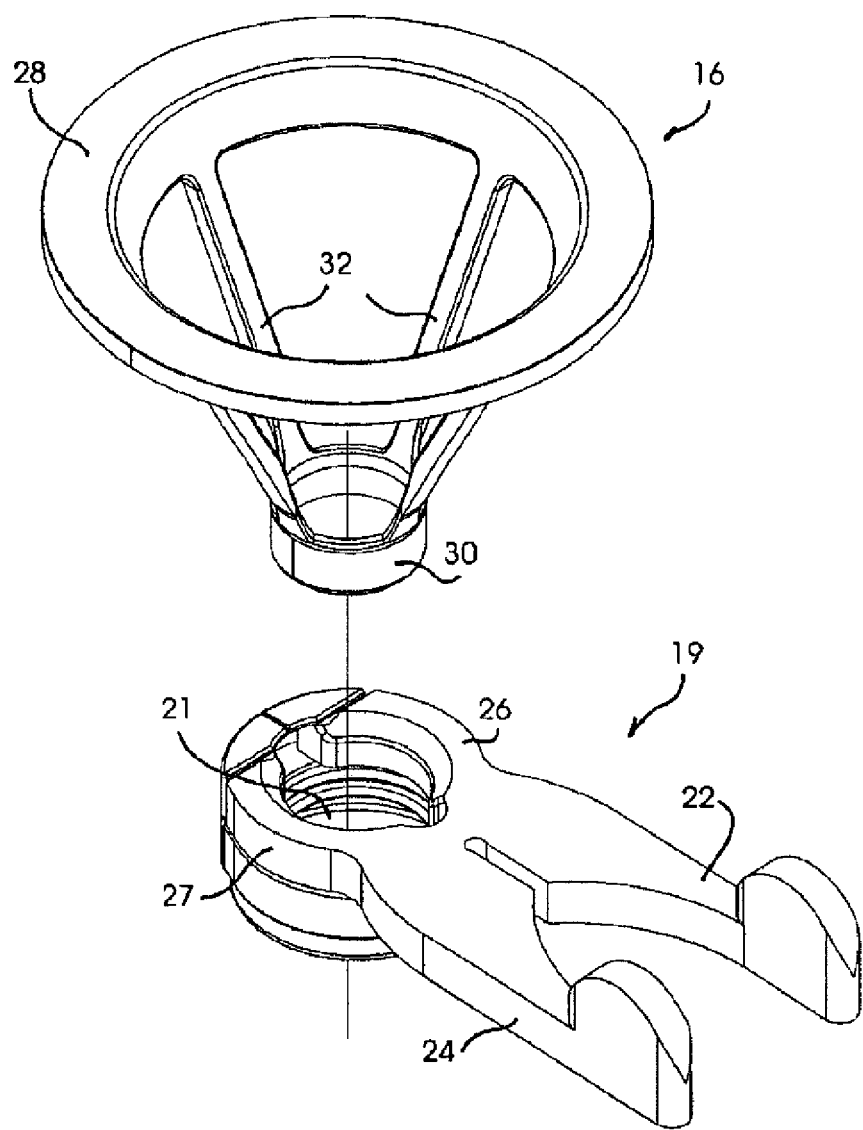
FIG. 4 is a perspective illustration of a lens cone, interfacing with a gripper/interface structure, and incorporating an applanation lens in accordance with the invention.

In this regard, and in connection with the perspective illustration of FIG. 4, the lens cone 16 is suitably constructed as an open-sided truncated cone-like structure, with an open, annular base ring 28 affixed to an open, cylindrical apex ring 30 by a set of support struts 32 which extend between the base ring 28 and the apex ring 30. The base ring 28 is larger than the apex ring 30 thereby giving the lens cone 16 its characteristic truncated cone-like shape.

Being cylindrical in construction, the apex ring 30 will be understood to comprise an inner diameter (ID) and an outer diameter (OD), wherein the OD is dimensioned such that it is only slightly larger than the ID of the central opening 21 of the gripper portion 19 of the gripper device 14. The lens cone 16 is constructed of a substantially rigid material such as a rigid, extruded plastic, aluminum, or the like, such that the OD of the apex ring 30 would not be expected to substantially deform under pressure, particularly not under the compression forces applied by the jaws 26 and 27 of the gripper portion 19.

Accordingly, the lens cone 16 would not precisely fit into the ID of the central opening 21 of the gripper device 14 under normal circumstances. However, once compressive force is applied to the lever handles 22 and 24, that force is applied to the remainder of the gripper device 14, causing the jaws 26 and 27 to open and the interior diameter of central opening 21 to increase in consequence. The OD of the apex ring 30 of the lens cone 16 is able to then be inserted into the central opening 21 of the gripper device 14 and, when pressure is released on the lever handles 22 and 24, the jaws 26 and 27 close upon the apex ring 30 thereby grasping the apex ring and establishing a fixed relationship between the lens cone 16 and the gripper device 14. Since the gripper device 14 is in geometric engagement with the attachment ring 12, and since the attachment ring 12 is coupled to corneal tissue, it should be understood that the lens cone 16 is now held in a particular spatial relationship (alignment) with the surface of the cornea.

As will be described in greater detail below, the apex ring 30 defines a receptacle for receiving and retaining an applanation lens 18. The applanation lens 18 is intended to be positioned in proximity with a human cornea and may be used to actually contact the cornea in some embodiments. The gripper device 14 functions to provide an alignment and coupling interface between the lens cone 16, including the applanation lens 18, and the attachment ring 12, and thereby the patient's eye. With regard to the laser delivery system, it will be understood that the base ring portion 28 of the lens cone 16 is adapted to be affixed to the distal end of a laser optical delivery system, such that the delivery system need only be concerned with focusing an incident laser beam at a particular point in space.

In one embodiment, the surface of the applanation lens 18 in contact with corneal tissue (the applanation surface) is disposed at a specific distance from the interface between the base ring and the laser delivery system, such that the anterior corneal surface, or at least that portion in contact with the applanation lens, is at a known specific distance from the laser delivery tip. The surface of the cornea now resides along a plane at a distance known to the laser.

Figure 5:
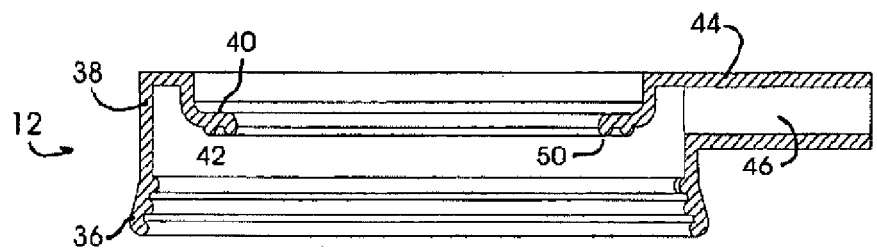
FIG. 5 is a simplified, cross-sectional illustration of an attachment ring, suitable for use in connection with the ocular stabilization device of FIG. 1.
Figure 6:
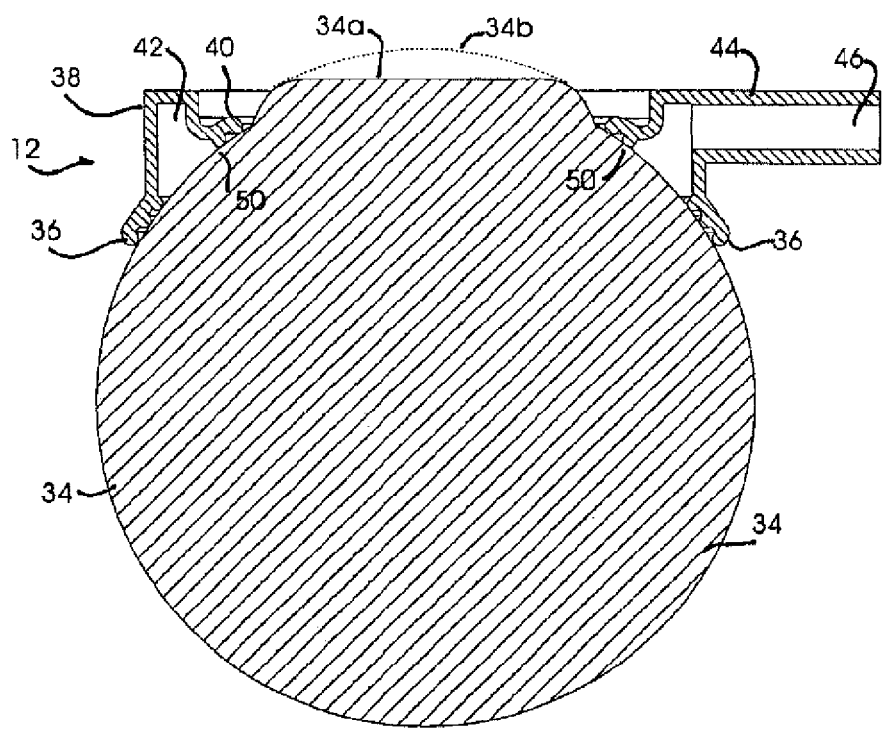
FIG. 6 is a simplified, cross-sectional illustration of the attachment ring of FIG. 5, illustrating the coupling of the attachment ring to the anterior surface of a patient's eye, and indicating applanation of the corneal surface in accordance with one embodiment of the present invention.

One embodiment of an attachment ring, generally indicated at 12, is illustrated in the cross-sectional diagrams of FIGS. 5 and 6, where FIG. 5 illustrates the attachment ring alone, and FIG. 6 illustrates the attachment ring as it would be applied to the anterior surface of a patient's eye. Recall that it is the function of the attachment ring 12 to provide a primary interface with an operative target, such as a human eye, and a laser delivery system. In this regard, the operative target is represented as the corneal portion 34a of a human eye 34 in the exemplary embodiment of FIG. 6, and to which the attachment ring 12 is illustrated as being affixed. In the exemplary embodiment of FIG. 5, the attachment ring 12 is illustrated as having an interior and exterior portion, the exterior portion of which is characterized by a lower skirt 36 which functions as a shroud that comes into intimate contact with the anterior portion of the human eye 34. The shroud 36 has a relatively thin cross-section and is deformable so as to establish and maintain conformal contact with the anterior corneal surface 52. The shroud or skirt portion 36 extends upwardly into a crown surface 38 which maintains a substantially uniform ID against deformations of the lower shroud portion 36 in response to pressure against the shroud portion by the human eye 34.

The attachment ring 12 further includes an interior, annular ring member 40 which is disposed on and protrudes outwardly from the interior surface of the attachment ring. The annular ring member 40 protrudes outwardly in a direction normal to the interior surface of the attachment ring, on its top surface, but is formed with a bottom surface that includes an upwardly extending cavity 42, with the cavity formed between a bottom portion of the annular ring member 40 and a proximate portion of the interior surface of the attachment ring 12. Thus, it should be understood that the cavity 42 formed by the shape of the annular ring member 40 defines an annular cavity, with its opening pointing towards the bottom, shroud or skirt portion of the attachment ring 12.

In the particular exemplary embodiment of FIGS. 5 and 6, the attachment ring 12 further includes an attachment fitting 44 which extends, in a radial direction, from the exterior surface of the attachment ring. The attachment fitting 44 includes a central orifice 46, disposed along its entire length, and which passes through the material of the attachment ring's skirt portion 36, such that a communication path is opened between the annular channel 42, at one end, and the distal end of the attachment fitting 44. The attachment fitting 44 might be constructed of the same material as the attachment ring 12, indeed the entire apparatus might be formed or molded as single piece. Alternatively, the attachment fitting 44 might be a separate small piece of plastic, metal, or some other material that is coupled to the attachment ring 12 at any stage in the manufacturing or assembly process of the stabilization device 10. It should also be noted that if the attachment fitting 44 were to be constructed from the same pliant, flexible rubber, silicone or plastic material as the attachment ring 12, a suitable female receptacle 72 (FIG. 11) can be provided on the underside of the gripper device 14 in proximity to and extending from the central opening 21 thereof. As the attachment ring 12 is friction-fit into place within the gripper device 14, the attachment fitting 44 is also press-fit into its corresponding female receptacle, thereby orienting and retaining the entire attachment ring structure within the gripper device 14, by compressive force.

Additionally, and as best shown in FIG. 1, the attachment fitting 44 might be accessed by inserting one side of a male-to-male fitting coupler 45 (FIG. 1) into the central orifice 46 and coupling the other side to a length of small diameter, medical grade tubing. The tubing is then coupled to a vacuum source which, in turn, is then able to apply a vacuum to the annular channel 42 through the attachment fitting 44. Alternatively, attachment ring 12 may be configured with projections, such as "teeth", "bumps", or some such other gripping or friction inducing structure, that would serve to attach the attachment ring to the eye without the need for suction.

In operation, and with regard to the particular embodiment of FIG. 6 42 which, in turn, couples the attachment ring 12 to the corneal surface 34a, thereby fixing the eye 34 to the attachment ring which, when it is itself coupled to the rest of the structure, as will be described in greater detail below, fixes the eye against relative movement, the attachment ring 12 is placed around the limbus of a patient's eye 34, such that its lower, skirt portion 36 surrounds the anterior surface of the cornea 34a, thereby leaving free optical access to the cornea 34a. In other embodiments, the attachment ring 12 has an ID of a dimension that permits placement of the attachment ring 12 around a portion of the sclera of a patient's eye 34. A slight compressive force is applied to the attachment ring 12, thereby deforming the skirt portion 36 in an outwardly direction, such that it tends to conform to the shape of the corneal surface. A slight vacuum is developed by a vacuum source or suction pump and coupled to the attachment ring 12 through the attachment fitting 44. As suction is applied to the attachment fitting 44, its internal orifice 46 couples the suction to the annular channel 42 which is now sealed-off from the external ambient environment by corneal, limbal, or scleral contact, or various combinations of ocular contact based on the foregoing (such as in off-centered coupling of the attachment ring 12 with the eye 34), with the skirt portion 36 (forming one side of the channel) and a contact edge 50 of the annular ring member 40 (forming the other surface of the channel). A vacuum is thereby developed within the annular channel It should be noted, in connection with the embodiment of FIG. 6, that in its preferred form, the attachment ring 12 is affixed to the gripper device 14, prior to the attachment ring being coupled to an eye. The gripper device 14 is not shown as being already attached to the attachment ring 12 in order that the particular structural and functional details of the attachment ring may be shown simply and without regard to additional and potentially confusing structure. Further, and as will be described in greater detail below, two corneal surface shapes are depicted in the illustrated embodiment of FIG. 6, a rounded surface 34a, indicating the normal shape of the cornea, and a flattened surface 34b indicating the effects of applanating the corneal surface. Applanation is discussed further in this specification, but it is worth noting that as the gripper device 14 is affixed to the eye 34, the structure surrounds the limbus, leaving the corneal area open to access, in one embodiment. The corneal surface remains substantially rounded, at this point, and may be contoured or flattened after introduction of the lens cone 16 into the gripper device 14 and contact is made between the applanation lens 18 and the cornea 34a. The applanated corneal surface 34b then takes on a shape imposed by the shape of the contact surface (applanation surface) of the applanation lens 18.

In the embodiment of FIG. 6, the vacuum or suction developed by the vacuum source or suction pump is transmitted to the attachment fitting 44 by small-bore tubing. The suction might be applied by coupling the tip of a syringe to the attachment fitting 44 and by introducing a vacuum in the body of the syringe. This vacuum is transmitted to the attachment ring 12 by a small-bore tubing, a blunt canula, or the like. All that is required is that a vacuum (partial or otherwise) be formed within the annular channel 42 such that it is able to provide a coupling force between the attachment ring 12 and the ocular surface.

Figure 7:
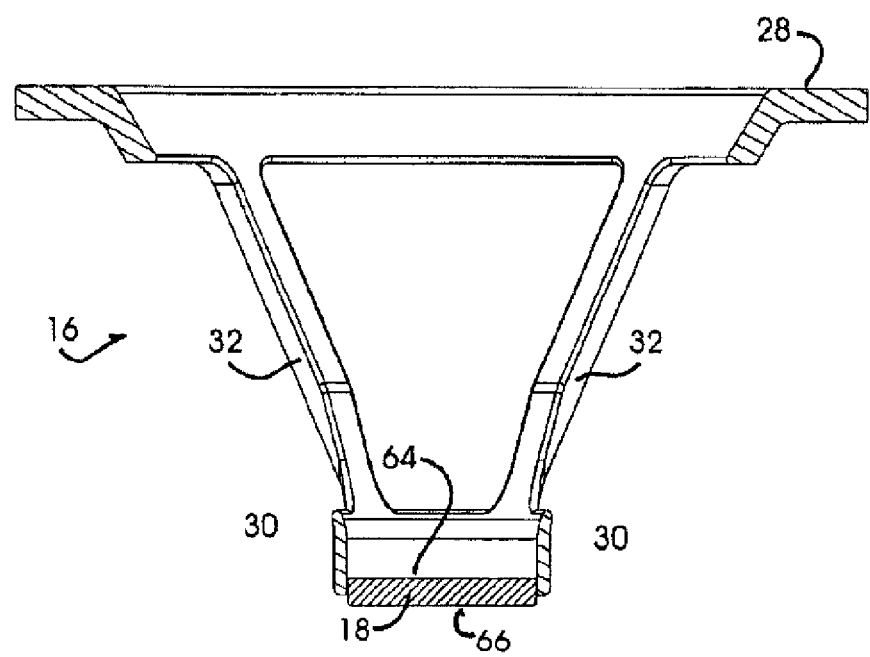
FIG. 7 is a simplified, cross-sectional illustration of a first embodiment of an applanation lens disposed within an attachment ring.

Turning now to FIG. 7, it will be appreciated that the lens cone 16 affords similar functionality to the attachment ring 12, in that the lens cone 16 provides the primary interface and attachment between the stabilization device (10 of FIG. 1) and the delivery tip of a surgical laser system. In this regard, the base ring 28 is rigidly coupled to the laser delivery system. Attachment between the two structures may be made in a number of ways, while remaining within the scope of the invention. In particular, the base ring 28 may be provided with slot-shaped cutouts which are mated with retaining pins provided on the delivery system, with the base ring being inserted over the pins and rotated in order to create an interlock. Alternatively, the base ring 28 can be screwed into place on the delivery tip or, the delivery tip might be provided with rotatable "dogs" which are rotated into place over the base ring 28 thereby securing the base ring into position. The means by which the base ring 28 and thus the lens cone 16 are affixed to the delivery tip is not particularly material to practice the principles of the invention. All that is required is that the lens cone 16 be affixed to the delivery tip such that it is incapable of independent relative movement with respect to the delivery tip. In this regard, it should be noted that the base ring has a top surface defining a generally horizontal plane (an x, y plane). The delivery tip is provided with a similar planar surface which is mated with the planar base ring surface. An x, y plane defining one aspect of ocular applanation is thereby established.

As illustrated in the cross-sectional diagram of FIG. 7, the lens cone's apex ring 30 extends downwardly away from the base ring 28 and is held in a particular spatial relationship by struts 32, extending between the apex ring 30 and the base ring 28. The base ring 30 is a substantially cylindrical structure with outer and inner wall surfaces and with a wall thickness sufficient to support reasonable rigidity under compressive stress. An applanation lens 18 is disposed within the apex ring 30 and has an OD substantially the same as the ID of the apex ring such that it fits into the apex ring and rests against the ring's interior wall surface. The applanation lens 18 is then bonded into place forming a generally unitary structure with the lens cone 16. The applanation lens 18 is formed with an anterior surface 64 and an applanation surface 66. It is to be appreciated that both the anterior surface 64 and the applanation surface 66 are substantially flat and substantially parallel to one another. The applanation lens 18 is suitably constructed from a quartz silicate glass or an optical quality plastic chosen for its transmission characteristics of light at the particular wavelength delivered by the laser system under consideration.

Manufacture of the lens cone 16 involves bonding and alignment of the applanation lens 18 to the apex ring 30. Both of these operations (bonding and alignment) are performed at substantially the same time. The lens cone 16 is placed in registration with an alignment and bonding fixture, termed a "golden pedestal". The golden pedestal has a horizontal alignment plane (an x, y plane) which is positioned parallel to the x, y plane defining the base ring 28. An applanation lens 18 is positioned on the golden pedestal such that its parallel anterior and applanation surfaces lie in the x, y plane defined by the pedestal and, thus the base ring. The lens cone is lowered over the lens until the lens is positioned within the apex ring portion, all the while maintaining the relationship between the various x, y planes. When the lens is in position, it is bonded, with a suitable glue, such as a UV curing cement, to the inside surface of the apex ring, thereby fixing the applanation lens in a specific plane, with respect to the base ring, and at a specific distance from the base ring. Accordingly, it will be appreciated that the applanation lens is established in a specific x, y plane and at a specific z distance from the base ring, itself established in a specific x, y plane and at a specific z distance from the delivery tip of a surgical laser. A known spatial relationship between the laser and the applanation surface of the applanation lens is thereby defined.

The applanation surface provides a reference surface from which the laser system is able to compute a depth of focus characteristic. In embodiments where the applanation surface contacts the corneal surface, since the position of the applanation surface is known, with respect to the delivery tip, so too is the position of the applanated corneal surface. It is, therefore, a relatively straightforward matter to focus a laser beam to any point within the cornea. One needs only to calculate the focal point with respect to the contact surface of the lens, in order that the same focal point be obtained within the eye.

Aligning the lens into position with respect to the lens cone by use of a "golden pedestal" allows alignment tolerances which are substantially tighter than those currently obtainable by conventional microkeratome techniques. Conventional microkeratomes typically exhibit off-plane errors in the range of about +/−30 to +/−40 microns. This alignment error can lead to planar tilt in the corneal flap, and to potential flap thickness variations. For example, if a flap were created with a 30 to 40 micron error, in the positive thickness direction, there exists the possibility that the remaining corneal bed would not be sufficiently thick to conduct a laser ablation procedure. Instead the cornea would tend to bulge outward, in response, leading to a less than optimum surface shape being presented for subsequent laser surface ablation.

In accordance with one embodiment of the invention, the "golden pedestal" registration and alignment system allows for planar (in both the x, y plane and the z direction) alignment tolerances no greater than that of a conventional microkeratome, i.e., in the range of about +/−30 microns, and preferably in the range of about +/−10 microns. This is measured with respect to both the planar "tilt" and the z position of the applanation surface of the applanation lens with respect to the defined plane of the base ring and, therefore, with respect to the laser's delivery tip. This is particularly advantageous when the applanation surface is devised to be co-planar with the anterior surface of the cornea, thereby defining a corneal surface that is mathematically calculable and precise with respect to the laser delivery tip: the x,y plane of the corneal surface is known, and the z distance from the tip to the surface is also known. Thus, a relatively precise cut may be made within the corneal material without concern for depth variation beyond desired pre-determined margins.

In other embodiments, tomography techniques (e.g, optical coherence tomography) or other ranging technology can be used to determine the relative location and position of various ocular structures, including the anterior corneal surface, the various corneal layers (e.g., epithelium, endothelium, Descemet's membrane, stroma, and Bowman's layer), the capsular bag, the lens, the retina, and the like. Using tomography or other ranging techniques, the relative location and position of the laser delivery tip with respect to such structures can be determined and thus, the depth of the laser beam can be determined and calibrated into acceptable tolerances equivalent to the aforementioned tolerances for alignment or tolerances associated with conventional microkeratomes. In such embodiments, the tolerances associated with the dimensions of the lens cone, alignment of the applanation lens, and the like, may have greater acceptable ranges.

Figure 8:
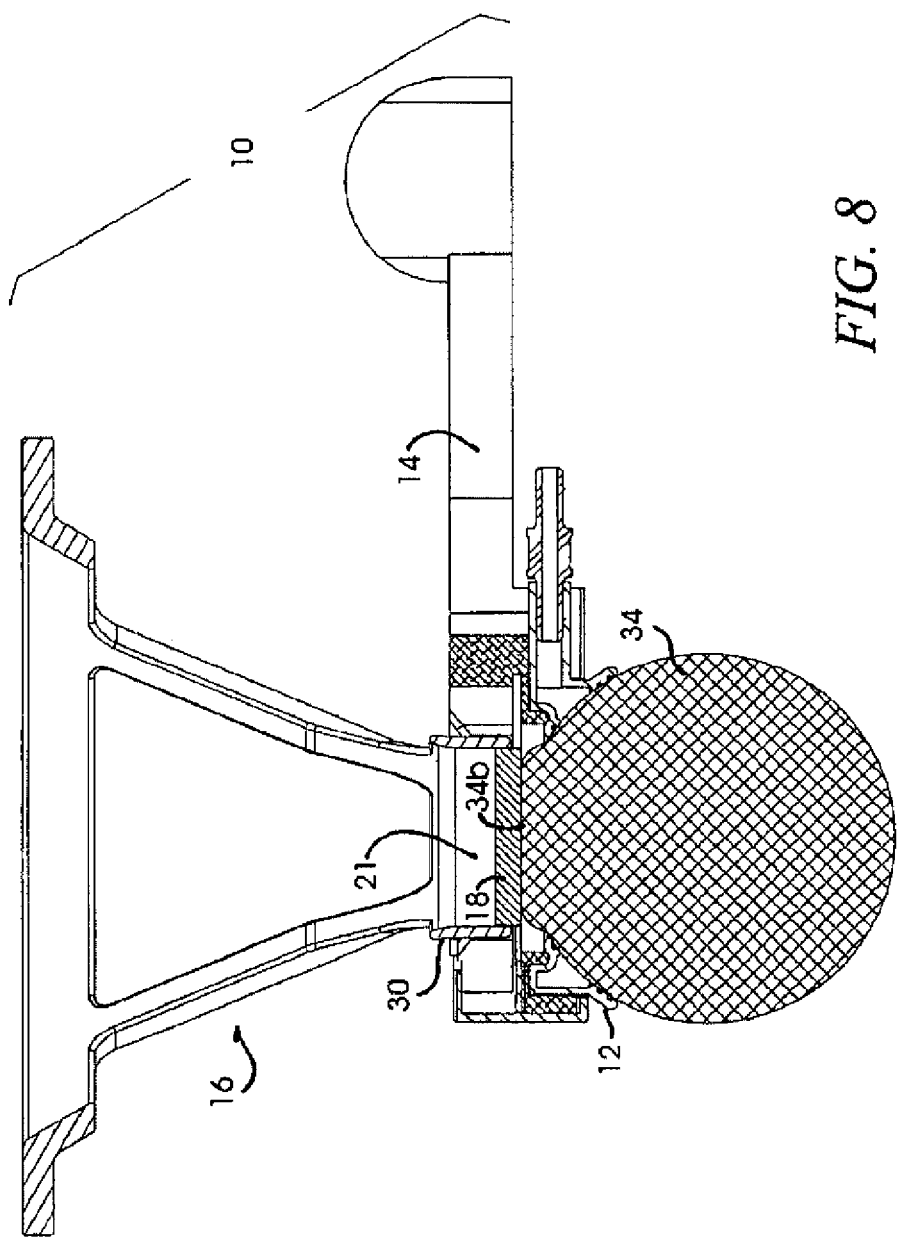
FIG. 8 is a simplified cross-sectional illustration of the ocular stabilization device of FIG. 1, showing operation of the device to applanate the corneal surface of an eye.

Turning now to FIG. 8, one embodiment of the complete ocular stabilization device 10, as it would be attached to a human eye, is illustrated in cross-sectional form. The lens cone 16 is coupled to the attachment ring 12, thereby coupling a patient's eye 34 to the laser delivery system, by interfacing the two structures together by the gripper device 14. As previously mentioned, the apex ring 30 has an OD sized just slightly larger than the ID of the gripper's annular mating portion 20, such that the apex ring 30 can be inserted into the central opening 21 of the gripper device 14, when the jaws 26 and 27 of the gripper device 14 are opened. The apex ring 30 is inserted into the central opening 21, pressure released on the gripping structures 22 and 24, thereby allowing the jaws 26 and 27 to relax and to close around and grip the apex ring 30 securely within the central opening 21.

In the embodiment shown in FIG. 8, as the apex ring 30 is inserted into the central opening 21 of the gripper device 14, the applanation surface 66 of the applanation lens 18 makes contact with a presented portion of the anterior surface of the cornea 34b. As the lens cone 16 is lowered into proximity with the cornea, the applanation surface of the lens makes contact with the cornea and applies a pressure to the cornea such that when the lens cone is lowered into position, the corneal anterior surface 34b and the applanation surface 66 of the lens are in intimate contact with one another over a substantial portion of the applanation surface.

Mechanical pressure of the lens causes the corneal surface to conform to the shape of the applanation surface of the lens. Although depicted in the embodiment of FIG. 8 as being flat, the cornea may be formed as a concave or convex surface, depending only on the shape of the contact surface of the applanation lens. The surface of the applanation lens 18 proximal to the cornea may be substantially planar, concave, convex, rigid, flexible, or any combination of the foregoing. For example, the applanation lens 18 may include a flexible membrane that is substantially transparent or has a refractive index that minimizes distortion or aberration of the laser beam.

In one embodiment, the attachment ring 12 is placed around the limbus of the eye, i.e., centered about the cornea and a pupillary aperture. The gripper device 14 has been previously affixed to the attachment ring 12, such that positioning the attachment ring with respect to the eye also positions the eye with respect to the gripper's central opening 21, with the pupillary aperture generally centered within the central opening. Suction is then applied to the attachment ring 12 in order to attach the ring onto the eye. With the eye so presented and held in place by the attachment ring 12, the lens cone 16 and applanation lens 18 can be lowered into proximity or actual contact with the cornea, and retain the lens cone, and particularly the applanation lens, in position by fixing the apex ring 30 with the gripper device 14. The gripper device 14 is opened to receive the lens cone 16 which is then lowered into the attachment ring 12. In one embodiment, the contact surface (applanation surface 66) of the applanation lens 18 can contact the corneal surface thereby applanating the cornea. The gripper device 14 is then closed, thereby clamping the lens cone 16 in position and fixing the applanation lens 18 relative to the cornea. The eye 34 is held to the gripper device 14 by the attachment ring 12, while the applanation lens 18 is held relative to the eye by the gripper device 14.

As should be understood from the foregoing, and with respect to the exemplary embodiments, the stabilization device is substantially rigidly coupled to the laser delivery system, thus the plane of the applanation surface 66 is characterizable in space with respect to any given focal point of an incident laser beam. With regard to the eye, it should be understood that the lens 18 is able to "float" in the "z"

direction due to the flexibility of the skirt portion of the attachment ring. The applanation lens 18 is therefore able to accommodate variously shaped corneal surfaces without placing undue pressure on the eye. Although able to "float" in the "z" dimension, the applanation lens 18 is secured against lateral motion and is accurately disposed in a stable "x,y" plane with respect to the eye.

Figure 9:
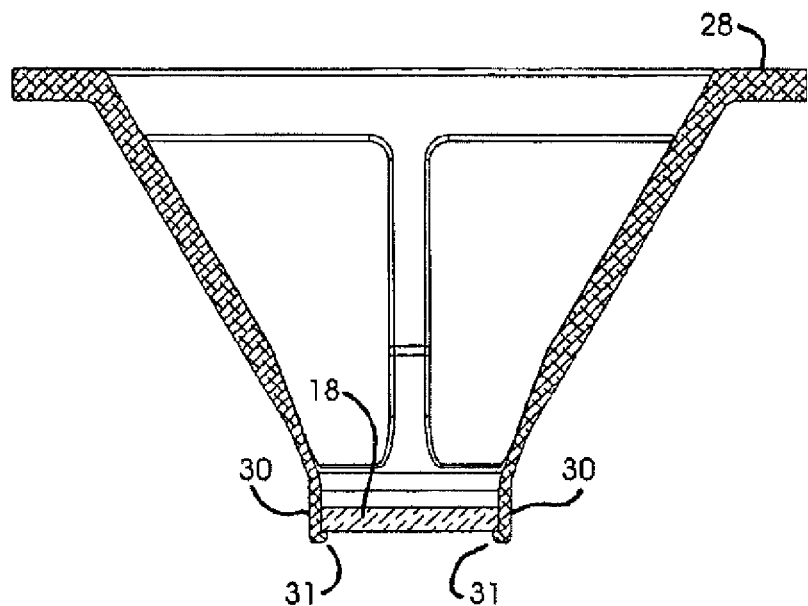
FIG. 9 is a simplified, cross-sectional illustration of a second embodiment of an applanation lens disposed within an attachment ring.

As an alternative embodiment, the applanation lens need not be affixed to the apex ring by a "golden pedestal" approach. As illustrated in the exemplary embodiment of FIG. 9, sufficient alignment of the lens 18 to the plane of the base ring 28 can be accomplished by machining the apex ring 30 to include a retaining lip 31 disposed around the bottom edge of the apex ring. The applanation lens 18 is inserted into the apex ring from the top, and allowed to rest against the retaining lip 31. The lens is now bonded into position using a suitable glue, such as an ultraviolet (UV) light curing cement. Likewise, the retaining lip 31 might be provided as an annular structure circumscribing the interior wall of the apex ring 30. The applanation lens 18 is inserted from the bottom until its anterior surface rests against the interior lip, at which position it is bonded into place. In one embodiment, the applanation lens 18 is positioned with respect to the lens cone 16 such that its alignment in the x, y plane and in the z direction is at least within an approximately +/−30 micron range. In other words, the applanation surface (and therefore the surface of the eye) is mathematically definable with regard to a laser delivery system to within about +/−30 microns.

An additional alternative embodiment will be appreciated by those having skill in the art, when it is considered that the applanation lens 18 might not be affixed to the lens cone 16 prior to the device being assembled on a patient's eye. The applanation lens 18 might be provided as a separate component from the lens cone structure. In this particular embodiment, the applanation lens is constructed as a shallow dish, with sides extending vertically upwards and having an OD such that it may be press-fit within the interior of the annular attachment ring. As the attachment ring and applanation lens combination is fixed to the corneal surface, the applanation lens is able to partially applanate the corneal surface in order to improve alignment. During the initial affixation and alignment procedure, the attachment ring may or may not be fitted within its appropriate receptacle in the gripper device 14. The attachment ring, either with or without the applanation lens included, might be first affixed on the patient's eye and the gripper device 14 lowered over the attachment ring, or, alternatively, the attachment ring, either with or without the applanation lens included, is press fit into its appropriate receptacle on the gripper device 14 and the entire composite placed over the surface of the patient's eye. In this particular instance, care must be taken to precisely manufacture the bottom surface of the apex ring 30, since this is the portion of the lens cone that now contacts the applanation lens 18. Contact pressure between the apex ring 30 and the applanation lens now steadies the lens in the desired plane. Needless to say, the attachment procedures described above hold true for any of the system embodiments described above, as well as one in which the applanation lens 18 is bonded directly to the gripper structure in a suitable position.

After the composite structure is either assembled on the patient's eye, or assembled and then positioned on the patient's eye, the lens cone 16 is lowered into position into the central opening 21 of the gripper device 14 and the jaws 26 and 27 of the gripper device are allowed to relax, thereby grasping and retaining the lens cone in position. As the lens cone 16 is lowered over the structure, final applanation can take place as the applanation lens is either further pressurized against the corneal surface by movement of the lens cone (if the applanation lens is provided as a separate structure) or as the applanation lens is moved into contact with the corneal surface, allowing cone pressure to applanate (if the applanation lens is provided within the lens cone's apex ring). In this regard, it is anticipated that ocular pressure developed by the applanation process will not exceed approximately 60 mmHg, and will preferably be in the range of about 40 to 50 mm Hg.

The lens cone 16 might be secured to the gripper device 14 in a number of ways, in addition to being gripped by compressive jaws. For example, the attachment ring might have a communication channel provided between the suction chamber and its interior surface. Accordingly, as the apex ring of the lens cone is lowered into engagement with the attachment ring, a suction is established between the attachment ring and the lens cone's apex ring thereby securing the lens cone to the attachment ring. Although suction involves a relatively simple application of force between the lens cone and attachment ring, suction (or vacuum) is not the only attachment methodology which is contemplated by practice of the invention. Indeed, the upper portion of the attachment ring might be provided with thin, magnetic material that attracts the lens cone's apex ring and provides for secured docking of the lens cone within the attachment ring. Further, the gripper device 14 might be provided with a suction manifold disposed around the central opening and the apex ring provided with a flange that overlays manifold openings. As the lens cone is lowered into position, and the flange covers the manifold openings, suction is applied thereby securing the lens cone to the gripper device 14. Accordingly, although mating between the lens cone 16 and the gripper device 14 has been described in connection with a flexible, press-fitted attachment, a vacuum attachment or a magnetic attachment, it should be understood that the only requirement is that the lens cone is securely held and maintained in a specific spatial relationship with respect to the attachment ring and, consequently, with the corneal surface.

Figure 10:
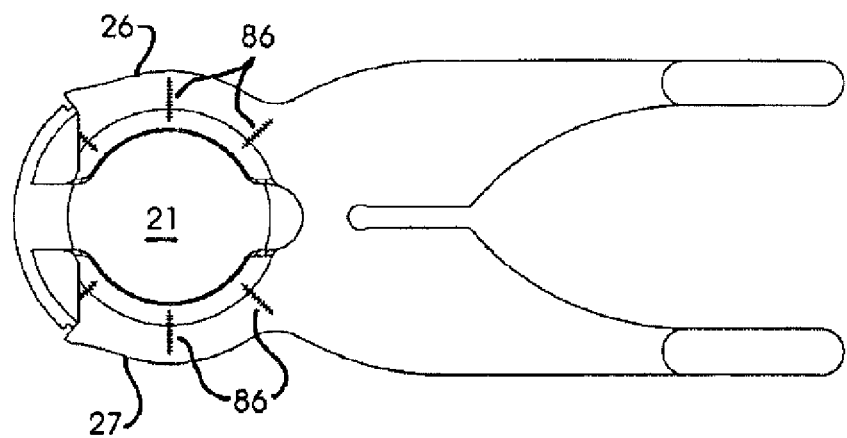
FIG. 10 is a simplified, semi-schematic illustration of the top surface of a gripper/interface device and showing radial alignment guides, in accordance with the present invention.

The present invention has been described, above, primarily with regard to aligning of the structure in relation to a human eye in the "z" dimension, while retaining the eye against relative motion along an "x, y" plane. It is also desirable to ensure proper alignment of the structure with regard to the central access of the eye, i.e., allow the structure to centrate about the pupil, such that the iris/pupil is positioned substantially in the center of the central opening of the attachment ring. Turning now to the semi-schematic, top plan view illustration of FIG. 10, the top surface of the gripper 14 (top being the surface opposite that in proximity with the eye) is provided with a set of alignment marks, or fiduciaries, radially disposed about the gripper's central opening 21, on the upper surface of each jaw 26 and 27 and surrounding the central opening 21. The fiduciaries are radially disposed and, if extended towards the center of the opening, aligned such that they will cross at the opening centrum or axis. The alignment marks allow a clinician to judge the central placement of an eye in relation to the opening and eases the clinician's task in accurately positioning the attachment ring/gripper device with respect to the ocular centrum, before the lens cone 16 is lowered into position in the central opening 21 of the gripper device 14. Once the lens cone 16 is in position, the already aligned gripper device 14 laterally aligns the applanation lens 18, in turn, to the eye. If the gripper device 14 is appropriately aligned such that the eye is substantially centered within the central opening 21, a nominal relationship will be established between a laser delivery system and the structural features of an eye in all directions (i.e., x, y, z). This simple mechanical approach obviates the need for complex, highly sophisticated eye following and tracking mechanisms.

Figure 11:
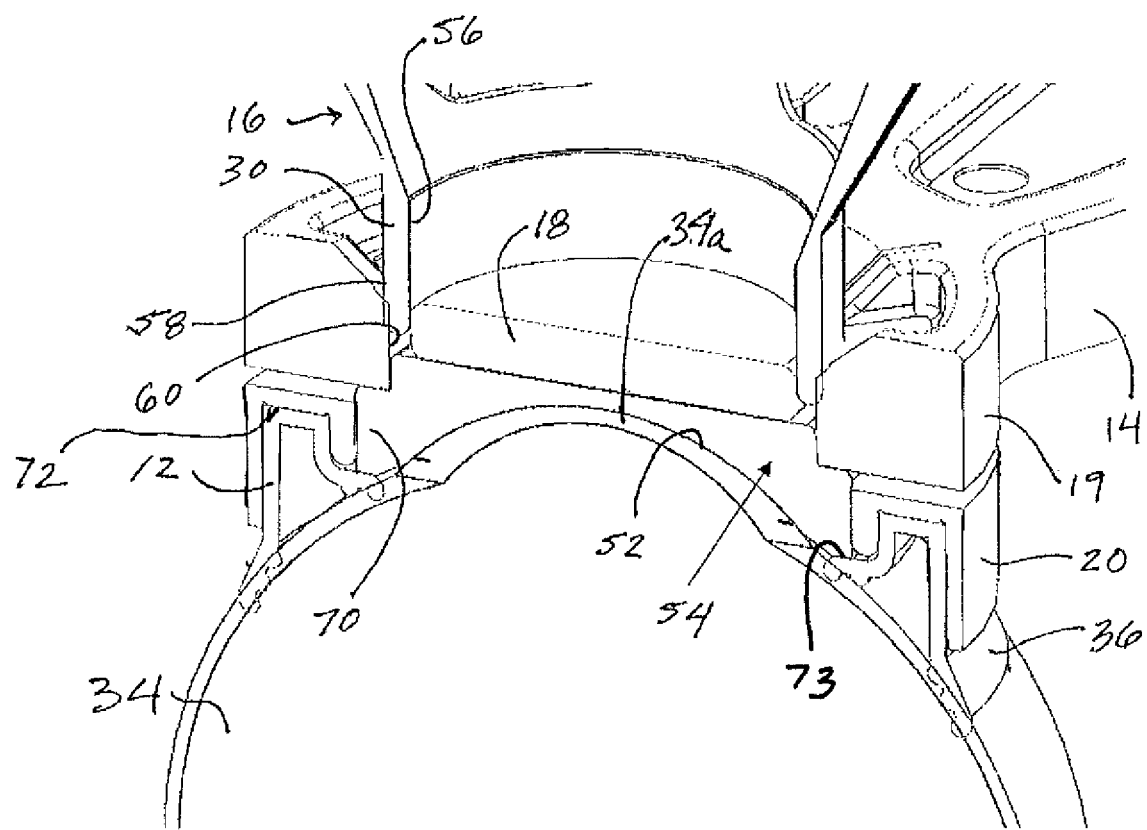
FIG. 11 is a cross-sectional illustration of the ocular stabilization and stabilization device of FIG. 1, showing operation of the device to interface with the corneal surface of an eye in accordance with one embodiment of the present invention.

An exemplary embodiment is shown in FIG. 11 illustrating an operation of the ocular stabilization device 10 to interface with the eye 34. For non-applanating applications of the ocular stabilization device 10, the lens cone 16 is coupled to the gripper device 14 without contact between the applanation lens 18 and the corneal portion 34a or with minimal contact, such as at point of first visible contact between the applanation lens and the corneal portion. In one embodiment, the lens cone 16 is coupled to the gripper device 14 such that the apex ring 30 of the lens cone is partially lowered into engagement with the attachment ring 18. In the embodiment shown in FIG. 11, an inner surface 60 of the gripper portion 19 of the gripper device 14, an inner surface 73 of the attachment ring 12, an inner surface 70 of the receiver portion 20 of the gripper device 14, and the applanation lens 18 form a chamber 54. As the gripper portion 19 includes the jaws 26 and 27, the inner surface of the gripper portion 19 is coextensive with the inner surface of the jaws 26 and 27, in one embodiment. Based on the position of the lens cone 16, and thus the position of the applanation lens 18, within the gripper portion 19 as well as the placement of the attachment ring 12 on the ocular surface, the chamber 54 can be formed without the inner surface of the gripper portion 10. For example, when the lens cone 16 is positioned within the gripper portion 19 such that the apex ring 30 engages all of the inner surface 60 of the gripper portion 19 without engaging the inner surface 70 of the receiver portion 19, the chamber 54 is formed by the applanation lens 18, the inner surface 70 of the receiver portion 20, and the inner surface 73 of the attachment ring 12. Thus, the dimensions of the chamber 54 can vary with the position of the lens cone 16 within the gripper device 14 but are fixed once the jaws 26 and 27 are compressed against the apex ring 30. Additionally, the chamber 54 is preferably not fluid-tight to allow displacement of the liquid material out of the chamber 54. In an exemplary embodiment of the present invention, a liquid 54 is provided in the chamber 54 such that any output beam from the laser delivery tip traverses through the applanation lens 18 and through the liquid to the eye 34 (e.g., the corneal portion 34a or other structures of the eye 34, such as the capsular bag, the natural lens, and the like).

Referring to the embodiment shown in FIG. 11, when the stabilization device 10 to the eye 34, after the attachment ring 12 is suctioned to the eye 34, such as via the annular channel 42 as previously described herein, a receptacle is formed by the anterior surface of the cornea, the inner surface 70 of the receiver portion 20, and the inner surface 60 of the gripper portion 19. In operation, a liquid or otherwise flowable material is then provided in this receptacle (e.g., by drops, injection, or the like). The lens cone 16 is subsequently docked to the gripper device 19 and displaced towards the corneal portion 34a. Alternatively, the liquid or otherwise flowable material may be provided in the receptacle after the chamber 54 is formed, such as after the lens cone 16 has been docket to the gripper device 19.

The liquid or otherwise flowable material is preferably biocompatible with the ocular tissue and substantially transparent or has a refractive index that substantially matches the refractive index of the corneal portion 34a. The incorporation of the liquid or otherwise flowable material between the applanation lens 18 and the corneal portion 34a minimizes trajectory departure of the output beam from the laser delivery tip to the desired ocular tissue structure or at least provides relative predictability to determine the trajectory departure, if any. Examples of suitable liquids, fluid-like suspensions or other compositions include but are not necessarily limited to basic salt solution, ophthalmic viscoelastic device, and the like, and any combination of one or more of the foregoing.

The exemplary embodiment shown in FIG. 11 describes a non-applanating application of the ocular stabilization device 10 that is particularly suited to laser assisted ophthalmic surgical procedures where minimizing change to intraocular pressure is desirable, such as in cataract procedures in older patients or patients with glaucoma-related or diabetic related complications. As previously mentioned, the chamber 54 is not fluid-tight. The liquid or otherwise flowable material may be displaced out of the chamber 54, such as from displacement of the applanation lens 18 towards the corneal portion 34a, after the gripper device 14 is affixed to the eye 34 and the lens cone 16 is docked with the gripper portion 19. This minimizes any external pressure that might be applied on the corneal portion 34a (and thereby any corresponding increase in intraocular pressure) due to displacement of the lens cone 16, and thus displacement of the applanation lens 18, towards the corneal portion 34a with the liquid material between the applanation lens 18 and the corneal portion 34a.

A number of exemplary embodiments suitable for practice of the present invention have been described in connection with various illustrations of FIGS. 1-11. However, it should be understood by those having skill in the art that certain modifications, simplifications and expansions may be made without departing from the spirit and scope of the present invention. Specifically, any appropriate laser medium might be used to deliver the incident laser beam without regard to the particular form and shape of the delivery system. In addition, the gripper structure need not be a unitary structure, for example, but may indeed be hinged in a central portion and the gripper jaws opened and closed in response to spring tension and compression made between the gripper handles. Likewise, the applanation lens need not be provided with a substantially flat applanation surface. Depending on the ophthalmic procedure intended to be carried out by the laser system, the lens's applanation surface may be concave or convex in accordance with an appropriate mathematically derived curvature, without departing from the scope and spirit of the invention.

In this particular regard, it will be understood that some degree of spherical aberration might be present in an uncompensated laser beam if the applanation surface of the applanation lens were curved. However, given the mathematical characterizability of the curvature of the applanation surface, it should be understood that a laser beam can be focus-compensated in order to accommodate a degree of curvature.

Accordingly, it is to be understood that the foregoing embodiments are merely illustrative of the invention and that no limitations are intended to either the details of the construction or design other than as defined in the appended claims.

What is claimed is:

1. A method for interfacing an eye to a surgical laser, the method comprising:
coupling a lens cone to a delivery tip of the surgical laser, the lens cone defining a first plane surface and the delivery tip being positionally referenced to the first plane surface, the lens cone comprising:
- an apex ring coupled to the first plane surface, the apex ring comprising a distal end; and
- an applanation lens disposed at a distal end of the apex ring and positioned in a second plane surface parallel to the first plane surface such that the delivery tip is positionally referenced to the second plane;

coupling an assembly including an attachment ring and a gripper to an anterior surface of the eye, the attachment ring having an inner surface, the gripper comprising:
- a second receptacle configured to receive the attachment ring, the second receptacle having an inner surface; and
- a central orifice configured to receive a lens cone,
- wherein the anterior surface of the eye, the inner surface of the attachment ring, and an inner surface of the central orifice of the gripper form a first receptacle;

after coupling the assembly to the anterior surface of the eye, receiving a liquid into the first receptacle;

after receiving the liquid into the first receptacle, positioning the distal end of the lens cone in the central orifice, including moving the distal end of the lens cone toward the anterior surface of the eye while displacing a portion of the liquid from the first receptacle, to a position where the applanation lens remains free of contact with the anterior surface of the eye; and thereafter, stabilizing the relative positions of the lens cone and the attachment ring with the gripper when the lens cone and the attachment ring are received within the gripper, a chamber containing the liquid being formed by the first receptacle and the applanation lens when the lens cone and the attachment ring are received within the gripper.

2. The method of claim 1, wherein the gripper includes two jaws around the central orifice, the jaws being configured to enlarge or reduce a size of the central orifice, wherein the positioning step is performed while the central orifice is enlarged by the jaws, and wherein the stabilizing step includes reducing the size of the central orifice to compress the lens cone disposed therein.

* * * * *